(12) United States Patent
Sugioka et al.

(10) Patent No.: US 7,618,531 B2
(45) Date of Patent: Nov. 17, 2009

(54) HEMODIALYSIS TREATMENT APPARATUS AND METHOD FOR HEMODIALYSIS TREATMENT

(75) Inventors: Akira Sugioka, Makinohara (JP);
Yoshihiro Mori, Makinohara (JP);
Masahiro Toyoda, Makinohara (JP)

(73) Assignee: Nikkiso Co., Ltd., Tokyo (JP)

( * ) Notice: Subject to any disclaimer, the term of this patent is extended or adjusted under 35 U.S.C. 154(b) by 594 days.

(21) Appl. No.: 11/424,393

(22) Filed: Jun. 15, 2006

(65) Prior Publication Data
US 2006/0289342 A1     Dec. 28, 2006

(30) Foreign Application Priority Data
Jun. 22, 2005    (JP) .............................. 2005-181721

(51) Int. Cl.
*B01D 61/30* (2006.01)
(52) U.S. Cl. ................ 210/85; 210/321.6; 210/646; 604/4.01
(58) Field of Classification Search ............... 604/4.01; 210/321.6, 85, 646
See application file for complete search history.

(56) References Cited

U.S. PATENT DOCUMENTS 7,297,129 B2 * 11/2007 Kinouchi et al. ........... 604/4.01

2005/0102165 A1 * 5/2005 Oshita et al. .............. 705/3

FOREIGN PATENT DOCUMENTS

| JP | 2004-97781 A | 4/2004 |
|----|-------------|--------|
| JP | 2004-248793 | 9/2004 |
| WO | WO-02053209 | 7/2002 |

OTHER PUBLICATIONS

Patent Abstracts of Japan for JP2004-97781 published on Apr. 2, 2004.

* cited by examiner

*Primary Examiner*—Terry K Cecil
(74) *Attorney, Agent, or Firm*—Darby & Darby P.C.

(57) ABSTRACT

A hemodialysis treatment apparatus includes a circulating blood volume variation rate detecting device, a vital sign detecting device and a display. The circulating blood volume variation rate detecting device detects a circulating blood volume variation rate of a patient in a time-course of a hemodialysis treatment. The vital sign detecting device detects a vital sign value of the patient in the time-course of the hemodialysis treatment. The display has a screen and displays both the circulating blood volume variation rate and the vital sign value on the screen along a time scale. The hemodialysis treatment apparatus dialyzes and ultrafiltrates extracorporeally circulating blood of the patient to perform the hemodialysis treatment.

10 Claims, 5 Drawing Sheets

HEMODIALYSIS TREATMENT APPARATUS AND METHOD FOR HEMODIALYSIS TREATMENT

INCORPORATION BY REFERENCE

The present application claims priority under 35 U.S.C. §119 to Japanese Patent Application No. 2005-181721 filed on Jun. 22, 2005, the entire contents of which are incorporated herein by reference.

BACKGROUND OF THE INVENTION

1. Field of the Invention

The present invention relates to an apparatus for hemodialysis treatment, which performs hemodialysis and ultrafiltration by extracorporeally circulating blood of a patient.

2. Discussion of the Background

A conventional apparatus for hemodialysis treatment includes a blood circuit, a dialyzer, a blood pump and a dialysis device. The blood circuit circulates blood of a patient extracorporeally, and is connected to the dialyzer. The dialysis device performs hemodialysis and ultrafiltration by having dialysate flow into and out from the dialyzer. The blood circuit has an arterial blood circuit provided with an arterial needle at an end thereof, and a venous blood circuit provided with a venous needle at an end thereof.

When the arterial needle and the venous needle are inserted to the patient, and the blood pump is turned on, blood of the patient flows through the arterial needle into the arterial blood circuit, the dialyzer and the venous blood circuit in sequence, and then flows back into the body of the patient through the venous needle. The dialyzer includes hollow fibers forming membranes for hemodialysis. The blood flows inside of the hollow fibers. The dialysate, which has a predetermined concentration and is supplied from the dialysis device, flows outside the hollow fibers (i.e., between outside surfaces of the hollow fibers and an inside surface of a case of the dialyzer). Waste products in the blood flowing in the inside of the hollow fibers permeate into the dialysate through the membranes.

The blood flows back to the body of the patient after flowing through the venous blood circuit and after the waste products being removed from the blood. Also, the dialysis device is provided with an ultrafiltration pump that removes water from the blood. The blood is also ultrafiltrated through the membranes during the hemodialysis treatment. A volume of water to be ultrafiltrated by the ultrafiltration pump (i.e., an ultrafiltration rate) is adjusted by controlling a driving rate of the ultrafiltration pump.

When an ultrafiltration volume (i.e., a volume of water to be ultrafiltrated) is large, it is necessary to increase the ultrafiltration rate. Consequently, the patient may show shock symptoms, such as a low blood pressure, depending on health conditions of the patient. Accordingly, the conventional apparatus monitors a sign of the shock symptoms during the hemodialysis treatment by detecting a hematocrit value of the blood of the patient (i.e., a ratio of a volume of red blood cells to a volume of whole blood), and by calculating a circulating blood volume variation rate (herein "$\Delta BV$") of the patient based on the hematocrit value, so as to predict the sign of such shock symptoms.

In this regard, although the $\Delta BV$ of the patient normally decreases due to the ultrafiltration in a time-course of the hemodialysis treatment, a sudden decrease in the $\Delta BV$ is considered to indicate the sign of the shock symptoms. Thus, it is possible to prevent an actual showing of the shock symptoms by performing a proper preventive treatment to the patient (e.g., additionally supplying saline and suspending the hemodialysis treatment) at the time the sudden decrease in the $\Delta BV$ occurs. The above described apparatus for hemodialysis treatment is described in the Japanese Patent Application Publication No. 2004-97781.

However, sudden changes in the $\Delta BV$ may also occur due to external events such as changes in the ultrafiltration rate and hemodialysis conditions, in body positions of the patient from lying down to sitting up on the bed, and in taking food and medications. In the above-described conventional apparatus, it is difficult to compare the $\Delta BV$ with vital signs of the patient (e.g., bio-information of the patient during the hemodialysis treatment, such as a blood pressure and a pulse) that indicate the occurrence of the external events. Therefore, it is difficult to effectively relate the sudden changes in $\Delta BV$ to the sign of the shock symptoms.

In this regard, a conventional apparatus having a display is available to independently display each of the $\Delta BV$ and the vital signs in a respective screen, one screen at a time on the display, thereby having a medical staff switch between multiple screens to monitor the $\Delta BV$ and the vital signs. Also, other conventional apparatuses are available, each dedicated to detect and display either the vital signs or the $\Delta BV$. Accordingly, a medical staff compares changes of the $\Delta BV$ and the vital signs displayed on multiple apparatuses to identify a cause of the sudden changes of the $\Delta BV$ when occurred. Consequently, when the above-described apparatus or apparatuses are used, because a medical staff is required to watch multiple screens independently by switching from one to another, or to shift the eyes between multiple apparatuses, the medical staff cannot efficiently and effectively monitor the $\Delta BV$ and the vital signs, thereby making difficult to determine whether the sudden changes in the $\Delta BV$ indicate the sign of the shock symptoms.

SUMMARY OF THE INVENTION

According to one aspect of the present invention, a hemodialysis treatment apparatus includes a circulating blood volume variation rate detecting device, a vital sign detecting device and a display. The circulating blood volume variation rate detecting device detects a circulating blood volume variation rate of a patient in a time-course of a hemodialysis treatment. The vital sign detecting device detects a vital sign value of the patient in the time-course of the hemodialysis treatment. The display has a screen and displays both the circulating blood volume variation rate and the vital sign value on the screen along a time scale. The hemodialysis treatment apparatus dialyzes and ultrafiltrates extracorporeally circulating blood of the patient to perform the hemodialysis treatment.

Because the display displays both the circulating blood volume variation rate and the vital sign value on the same screen along the time scale, the circulating blood volume variation rate and the vital sign value are efficiently and effectively compared when the sudden changes in the circulating blood volume variation rate occur. As a result, it is efficiently and effectively determined whether such sudden changes is the sign of the shock symptoms.

According to another aspect of the present invention, a method for hemodialysis treatment includes dialyzing and ultrafiltrating extracorporeally circulating blood of a patient to perform a hemodialysis treatment. A circulating blood volume variation rate of the patient is detected in a time-course of the hemodialysis treatment. A vital sign value of the patient is detected in the time-course of the hemodialysis treatment. Then, both the circulating blood volume variation rate and the vital sign value are displayed on a screen of a display along at least one time scale.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
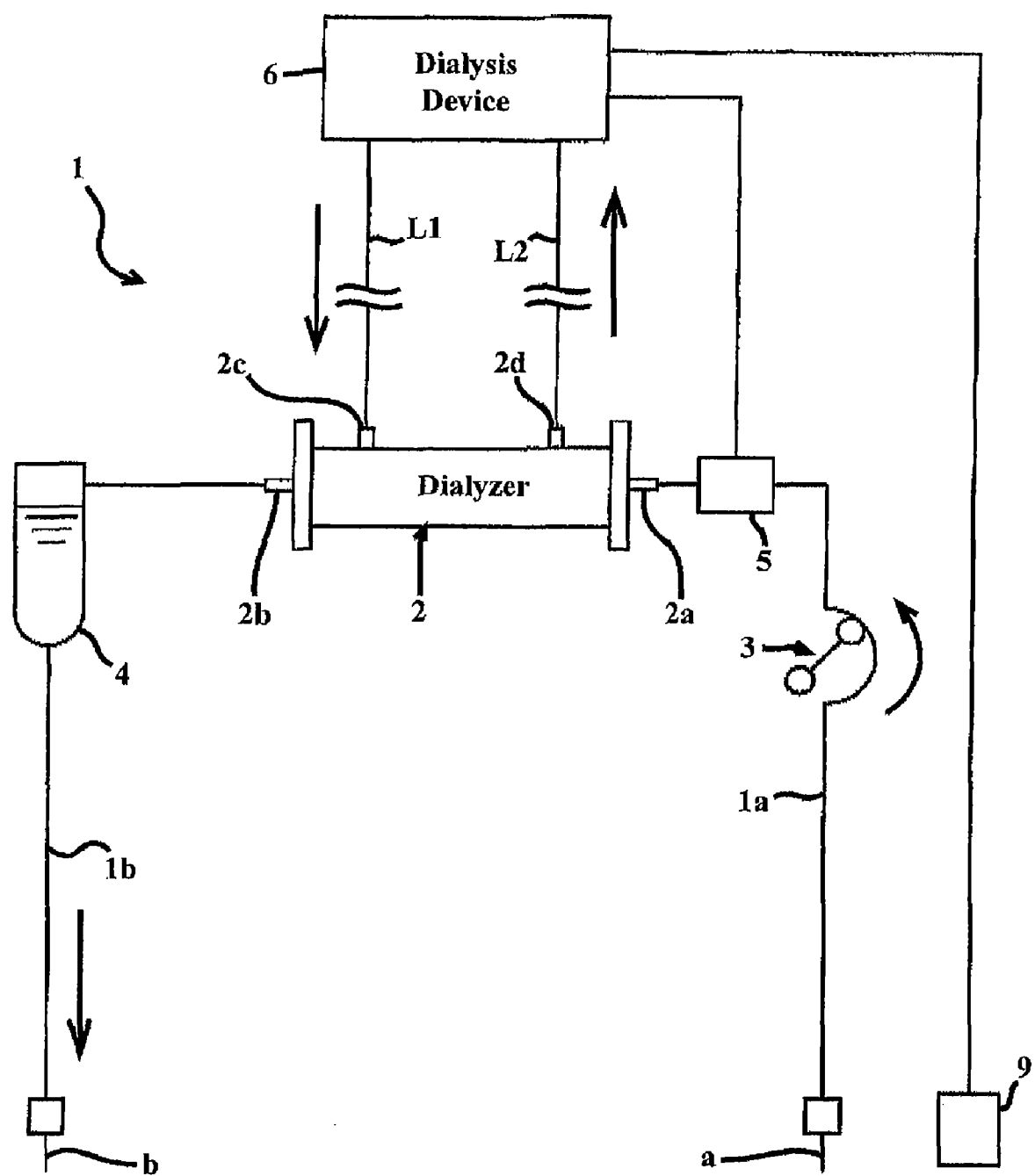
FIG. 1 is a schematic diagram of a hemodialysis treatment apparatus according to an embodiment of the present invention.

The embodiments will now be described with reference to the accompanying drawings, wherein like reference numerals designate corresponding or identical elements throughout the various drawings.

A hemodialysis treatment apparatus according to the present invention is used to perform hemodialysis and ultrafiltration by extracorporeally circulating blood of a patient. FIG. 1 is a schematic diagram of the hemodialysis treatment apparatus that includes a blood circuit 1, a dialyzer 2 and a dialysis device 6. As shown in FIG. 1, the blood circuit 1 is provided with an arterial blood circuit 1a and a venous blood circuit 1b each made from flexible tubing, and circulates the blood of the patient. The dialyzer 2 is connected to the blood circuit 1 between the arterial blood circuit 1a and the venous blood circuit 1b and performs hemodialysis. The dialysis device 6 is connected to the dialyzer 2 to supply dialysate and to ultrafiltrate the blood.

The arterial blood circuit 1a is provided at an end thereof with an arterial needle a, and also provided therealong with a blood pump 3 and a hematocrit sensor 5. The venous blood circuit 1b is provided at an end thereof with a venous needle b, and also provided therealong with a venous drip chamber 4 to remove air bubbles.

The hematocrit sensor 5 has a photo emitter (e.g., a light emitting diode) and a photo detector (e.g., a photo diode), and measures a hematocrit value indicating a concentration of the blood. Specifically, the hematocrit sensor 5 measures the hematocrit value by emitting a light with a predetermined wave-length to the blood from the photo emitter, and detecting either a transmitted or reflected light by the photo detector. The hematocrit value indicates a ratio of a volume of red blood cells to a volume of whole blood.

When the blood pump 3 is turned on while the arterial needle a and the venous needle b are inserted to the patient, the blood of the patient flows through the arterial blood circuit 1a into the dialyzer 2 that dialyzes the blood. Subsequently, the blood returns to the body of the patient through the venous blood circuit 1b after bubbles are removed by the venous drip chamber 4. Thus, the blood is dialyzed by the dialyzer 2 during extracorporeal circulation through the blood circuit 1.

The dialyzer 2 is provided with a blood inlet port 2a, a blood outlet port 2b, a dialysate inlet port 2c and a dialysate outlet port 2d. The blood inlet port 2a and the blood outlet port 2b are each connected to ends of the arterial blood circuit 1a and the venous blood circuit 1b, respectively. Additionally, a dialysate inlet line L1 and a dialysate outlet line L2 are each extended from the dialysis device 6, and are each connected to the dialysate inlet port 2c and the dialysate outlet port 2d, respectively.

The dialyzer 2 includes a plurality of hollow fibers. The blood flows inside the hollow fibers, and the dialysate flows between outside surfaces of the hollow fibers and an inside surface of a case of the dialyzer 2. The hollow fibers are provided with a plurality of micropores on the inside and outside surfaces of the hollow fibers. This forms permeable membranes which allow waste products in the blood to permeate into the dialysate.

Figure 2:
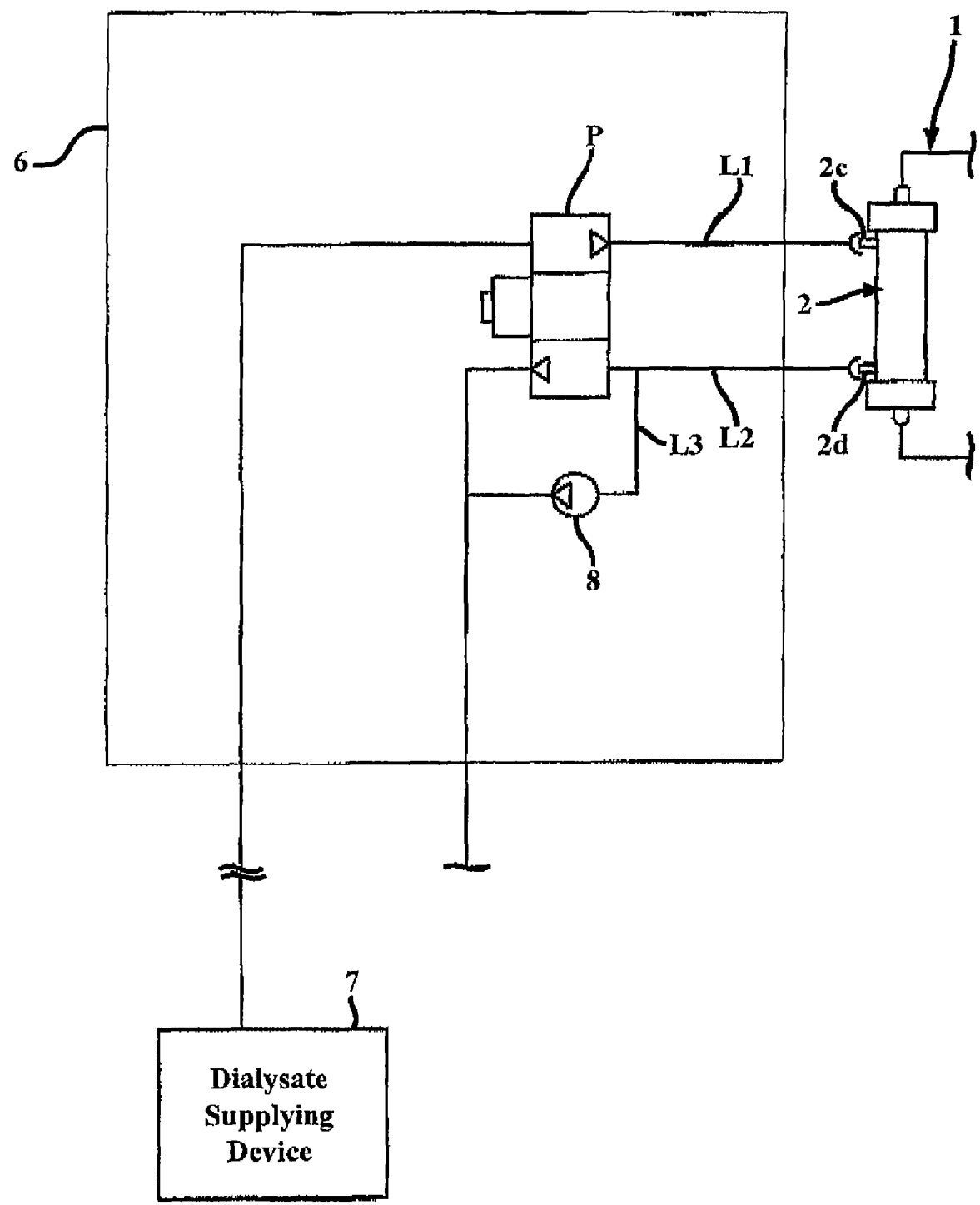
FIG. 2 is a schematic diagram of a dialysis device in the hemodialysis treatment apparatus according to the embodiment of the present invention, showing an internal structure of the dialysis device.

FIG. 2 is a schematic diagram showing a mechanical structure of the dialysis device 6 in the hemodialysis treatment apparatus. As shown in FIG. 2, the dialysis device 6 includes a duplex pump P, a bypass line L3 and an ultrafiltration pump 8. The duplex pump P is connected to both the dialysate inlet line L1 and the dialysate outlet line L2, bridging the two lines L1 and L2. The bypass line L3 is connected to the dialysate inlet line L2 bypassing the duplex pump P, and is also connected to the ultrafiltration pump 8. The dialysate inlet line L1 is connected at one end thereof to the dialysate inlet port 2c of the dialyzer 2, and at another end thereof to a dialysate supplying device 7 that adjusts the dialysate to a predetermined concentration.

The dialysate outlet line L2 is connected at one end thereof to the dialysate outlet port 2d of the dialyzer 2, and at another end thereof to a fluid disposal device (not shown). The dialysate supplied from the dialysate supplying device 7 flows through the dialysate inlet line L1 into the dialyzer 2, then, flows through the dialysate outlet line L2 and the bypass line L3 into the fluid disposal device.

The ultrafiltration pump 8 ultrafiltrates the blood to remove water from the blood flowing in the dialyzer 2. When the ultrafiltration pump 8 is activated, a volume of the dialysate flowing out from the dialysate outlet line L2 becomes greater than a volume of the dialysate flowing in through the dialysate inlet line L1 because the duplex pump P is quantitative. Accordingly, water is removed from the blood by the difference between the volumes flowing out and flowing in. Devices other than the ultrafiltration pump 8 (e.g., a balancing chamber) may be used to ultrafiltrate the blood. Further, the dialyzer 2, the duplex pump 3 and the ultrafiltration pump 8 together form a dialyzing device in the hemodialysis treatment apparatus, which performs the hemodialysis and the ultrafiltration by extracorporeally circulating the blood of the patient.

The dialysis device 6 is electrically connected to a vital sign detecting device 9. The vital sign detecting device 9 is placed onto the patient to detect vital signs, such as a blood pressure and a pulse, of the patient in a time-course of a hemodialysis treatment, and to output vital sign values to the dialysis device 6. The vital signs refer to bio-information of the patient taking the hemodialysis treatment, and may include, in addition to the blood pressure and the pulse, a breath, a body temperature, an oxygen saturation and a perspiration rate.

Figure 3:
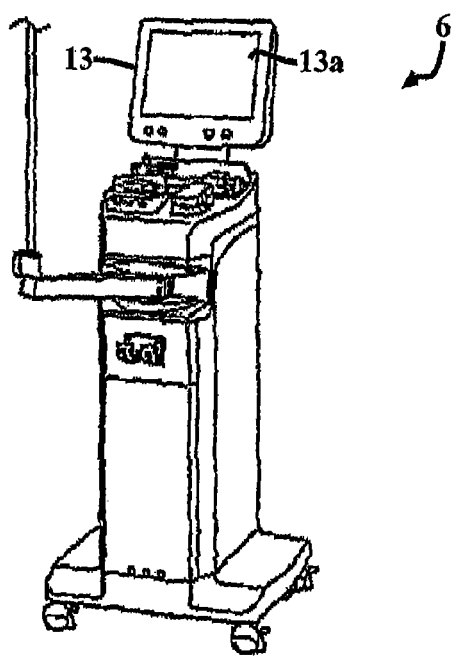
FIG. 3 is an exterior perspective view of the dialysis device according to the embodiment of the present invention.
Figure 4:
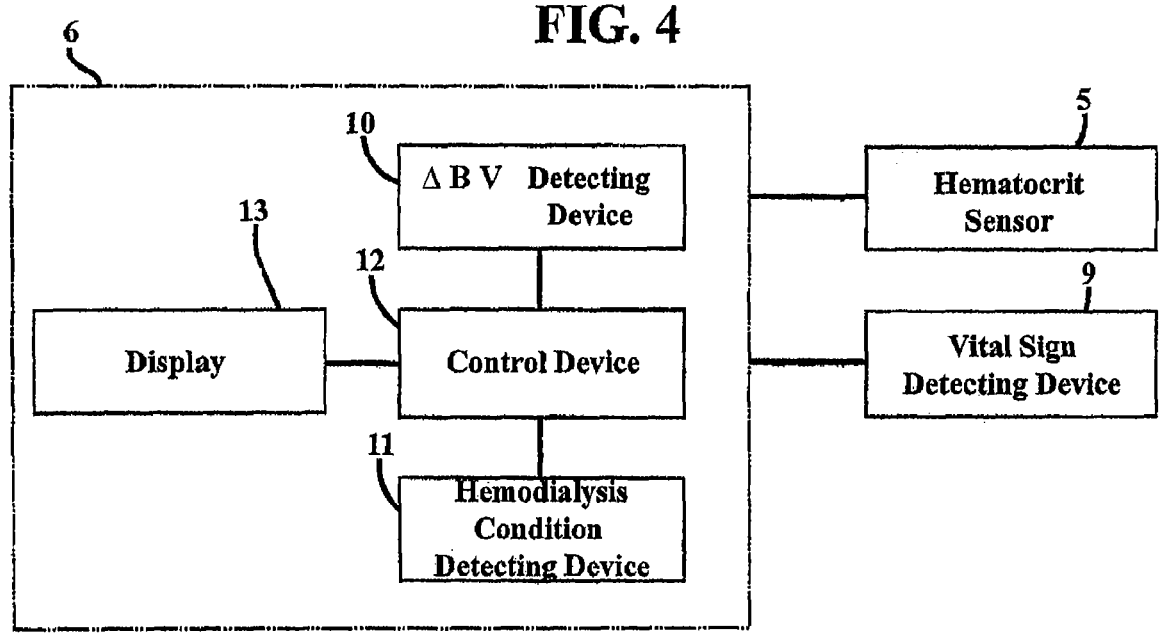
FIG. 4 is a block diagram of the dialysis device according to the embodiment of the present invention, showing an internal structure of the dialysis device.

FIG. 3 is an exterior perspective view of the dialysis device 6 provided with a display 13 that displays data of a current hemodialysis treatment (e.g., a duration of time passed and a ultrafiltration rate) on a screen 13a that is a touch panel screen. FIG. 4 is a block diagram of the dialysis device 6, showing an internal structure thereof. The display 13 is electrically connected to a control device 12 that is connected to a circulating blood volume variation rate detecting device (herein "ΔBV detecting device") 10 and a hemodialysis condition detecting device 11.

The ΔBV detecting device 10 is electrically connected to the hematocrit sensor 5 to calculate and detect a circulating blood volume variation rate ΔBV based on the hematocrit value sent from the hematocrit sensor 5. In this regard, the ΔBV is obtained by the following formula where the Ht represents the hematocrit value obtained by the hematocrit sensor 5.

{(Ht at the start of the hemodialysis treatment–Ht at the time of detecting the ΔBV)/Ht at the time of detecting}×100

Accordingly, the ΔBV is detected as required during a time-course of the hemodialysis treatment.

The hemodialysis condition detecting device 11 detects, as required, hemodialysis conditions relating to hemodialysis and ultrafiltration in a time-course of the hemodialysis treatment (e.g., an ultrafiltration rate and a venous blood pressure obtained by detecting an air-layer side internal pressure of the venous drip chamber 4 provided along the venous blood circuit 1b). Values detected by the hemodialysis condition detecting device 11, the ΔBV detecting device 10 and the vital sign detecting device 9 are sent to the control device 12 to be processed and displayed at the display 13.

Figure 5:
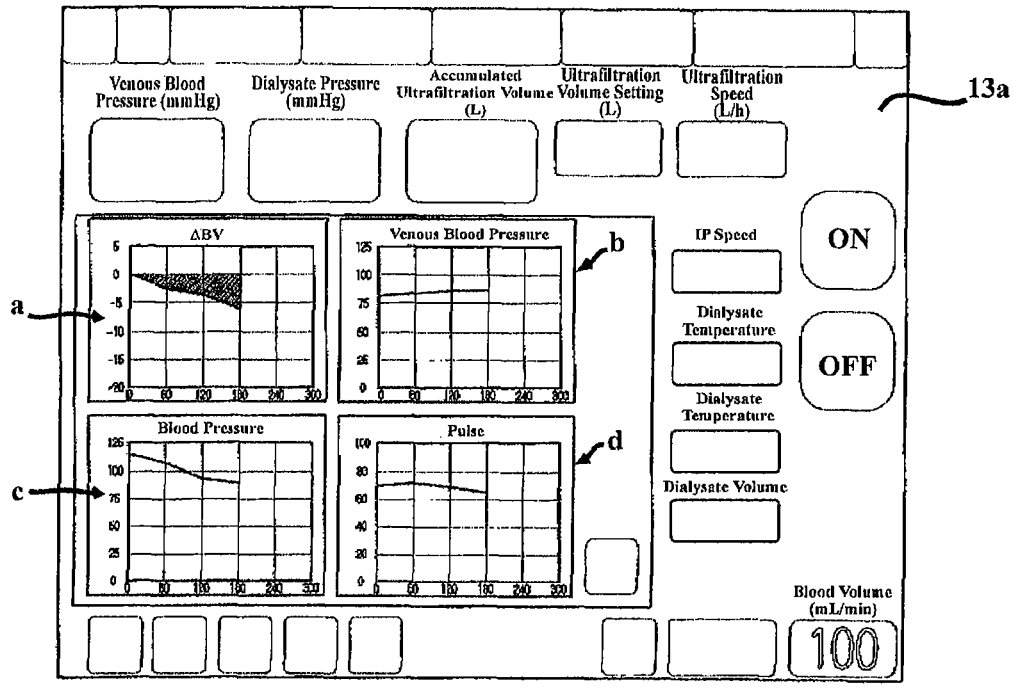
FIG. 5 is a schematic diagram of a screen of a display provided at the dialysis device of the embodiment of the present invention.

Specifically, the control device 12 controls the values detected by each of the above-described detecting devices (i.e., the vital sign detecting device 9, the ΔBV detecting device 10 and the hemodialysis condition detecting device 11) so that the screen 13a of the display 13 displays those values in graphs a, b, c and d aligned in parallel by time axes of the graphs as shown in FIG. 5. Each of the time axes is a horizontal axis indicating elapsed time from the start of the hemodialysis treatment. Also, the screen 13a displays additional data of the current hemodialysis treatment, including a dialysate pressure, an accumulated ultrafiltration volume and a dialysate temperature. Displaying, in a graph or a chart, elapsed time from the start of the hemodialysis treatment and changes in detected values is hereinafter referred to a "time axis display."

For example, the graph a is obtained by plotting, along the time axis, ΔBVs detected by the ΔBV detecting device 10. The graph b is obtained by plotting, along the time axis, venous blood pressures detected by the hemodialysis condition detecting device 11. The graphs c and d are obtained by plotting, along the time axis, blood pressures and pulses. Because the screen 13a displays the graphs a, b, c and d at the same time, aligning them in parallel by the time axes, changes in the values in the graphs are monitored and compared to each other visually and effectively.

According to the embodiment of the present invention, the values detected by the ΔBV detecting device 10 and by the vital sign detecting device 9 are together displayed on a single screen (i.e., the screen 13a) aligned by the time axes. Thus, when the ΔBV suddenly decreases during the hemodialysis treatment, the ΔBV is effectively compared to the vital signs (e.g., the blood pressure and the pulse) to determine whether the sudden decrease in the ΔBV is a sign indicating shock symptoms of the patient.

In addition to the values detected by the ΔBV detecting device 10 and by the vital sign detecting device 9, the values detected by the hemodialysis condition detecting device 11 (e.g., the venous blood pressure in the above-described embodiment) are also displayed on the same screen (i.e., the screen 13a) in the graph b having the time axis aligned with the time axes of the graphs a, c and d indicating the values detected by the ΔBV detecting device 10 and the vital sign detecting device 9. Thus, when the ΔBV suddenly decreases during the hemodialysis treatment, the ΔBV is effectively compared to the hemodialysis conditions to determine whether the sudden decrease in the ΔBV is due to changes in the hemodialysis conditions. In this regard, as long as the graph a indicating ΔBV is on display, one or more of other graphs indicating values of the vital signs and the hemodialysis conditions may be optionally displayed.

According to another embodiment of the present invention, a hemodialysis treatment apparatus, which also performs hemodialysis and ultrafiltration by extracorporeally circulating blood of a patient, is provided with a control device that controls a display on the display 13 differently from the control device 12 in the above-described embodiment. The control device in the another embodiment controls the display 13 so that the values, which are detected by the detecting devices including the vital sign detecting device 9, the ΔBV detecting device 10 and the hemodialysis condition detecting device 11, are displayed on a single screen in graphs on a single grid sharing a single time axis.

For example, the graph a is obtained by plotting along the time axis ΔBVs detected by the ΔBV detecting device 10. The graph e is obtained by plotting along the time axis ultrafiltration speeds detected by the hemodialysis condition detecting device 11. The graph c is obtained by plotting along the time axis blood pressures detected by the vital sigh detecting device 9. Because the screen 13a displays the graphs a, c and e on the single screen on the single grid sharing the single time axis, changes in the values in the graphs are monitored and compared to each other visually and effectively.

Further, according to this embodiment, because the values are compared to each other visually on the single grid, a cause of the sudden decrease in the ΔBV are effectively identified. Also, a different display color may be used for each of the graphs so that the graphs are compared to each other more visually.

According to this embodiment, the screen 13a may display only graphs selected from available graphs. For example, when the graph a indicating the ΔBV and the graph c indicating the blood pressure are selected to be displayed, other graphs (e.g., the graph e indicating the ultrafiltration speed) may be turned off from display. Accordingly, because selected graphs are efficiently displayed on the display 13 so as to be visually recognized better, changes in the values selected to be displayed are compared to each other efficiently and effectively thereby making a hemodialysis treatment analysis effective.

Further, according to this embodiment, the screen 13a displays a function key A indicated as "Event." By touching the function key A, an external event that affects the hemodialysis treatment for the patient, and a time that external event occurs are input and displayed on the display 13. Such external event includes a factor that may affect the ΔBV, such as changes in body positions of the patient (e.g., changing from lying to sitting up on the bed), and taking medications or food.

Figure 6:
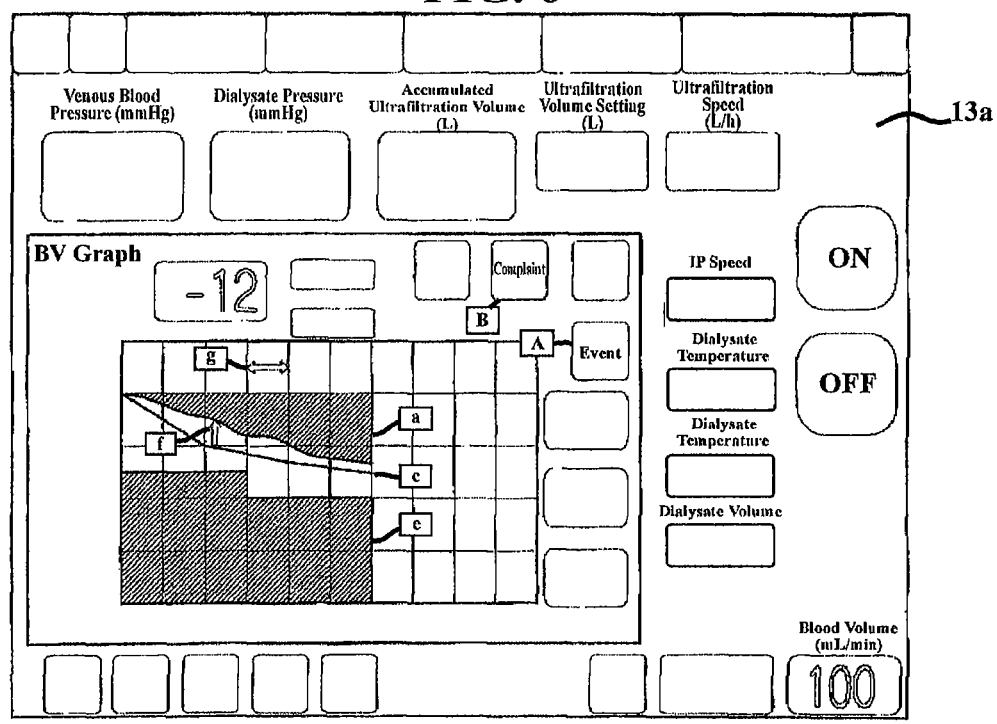
FIG. 6 is a schematic diagram of a screen of a display provided at a dialysis device of another embodiment of the present invention.

For example, as shown in FIG. 6, when a medical staff inputs, by touching the function key A, the changes in the body positions of the patient, an arrow f is indicated along the time axis at the time the changes occurred. Also, when the medical staff inputs, by touching the function key A, a factor that the patient takes a medication for a duration of time, an arrow g is indicated along the time axis at the time and for the duration of the taking of the medication occurred. The arrow g may be indicated by touching and retouching the function key A at the time the patient starts and stops taking the medication, respectively. Alternatively, the arrow g may be indicated by touching the function key A at the time the patient starts taking the medication and inputting the ending time of taking the medication. Further, such arrow indicating the external event may be displayed with a numerical reference or icon, or replaced with another symbol, to inform the medical staff whether the arrow indicates the changes in the body positions of the patient or the taking of the medication.

Accordingly, because the time and the duration of the occurrence of the external event, which affects the hemodialysis treatment of the patient, are displayed on the screen 13a, the values along the time axis are effectively compared to the occurrence of such external event. Thus, when the sudden decrease in the $\Delta$BV occurs, an analysis is efficiently and effectively performed whether such sudden decrease is due to the external event. Moreover, the screen 13a displays a function key B indicated as "Complaint." By touching the function key B, complaints by the patient (e.g., nausea and headache) are input and displayed on the display 13.

Figure 7:
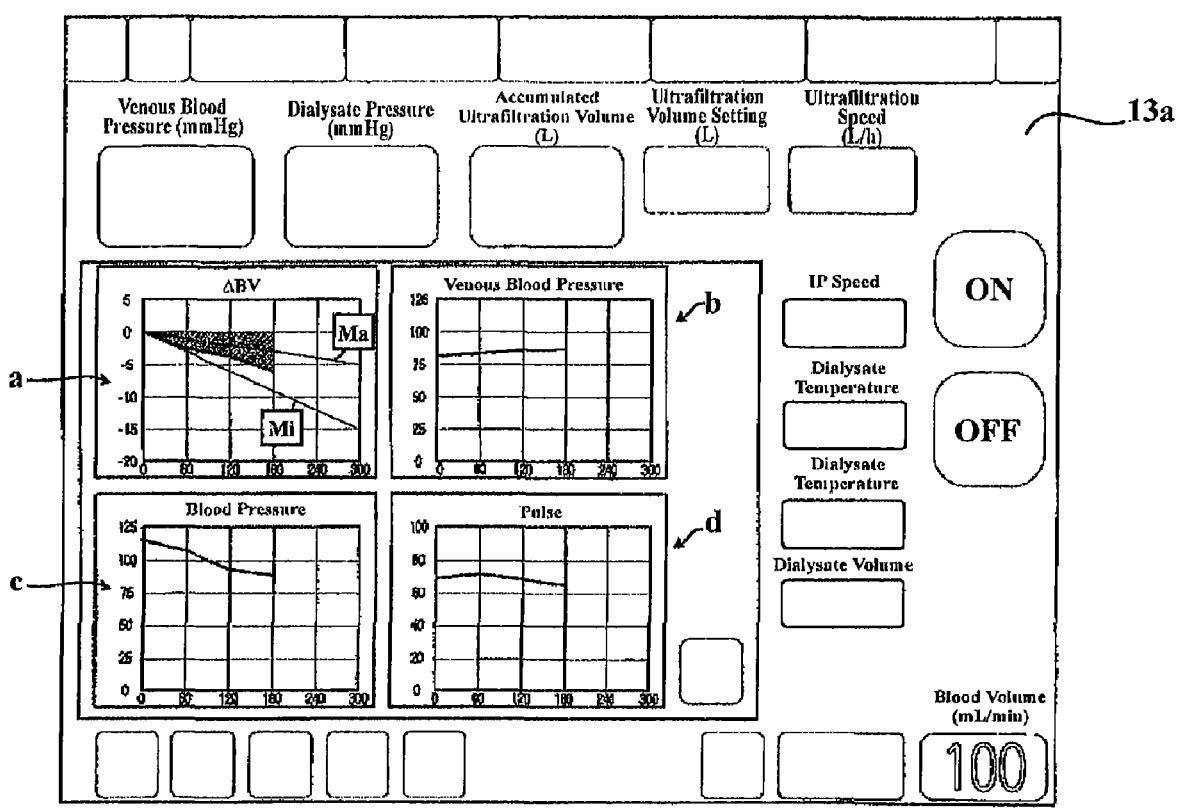
FIG. 7 is a schematic diagram of a screen of a display provided at a dialysis device of yet another embodiment of the present invention.

The present invention is not limited to the above-described embodiments. For example, the hemodialysis treatment apparatus may be provided with a memory that stores prior detected values detected by the $\Delta$BV detecting device 10 in a prior hemodialysis treatment. As illustrated in FIG. 7, prior detected values may be plotted along the time axis in the grid indicating other values detected by the $\Delta$BV detecting device 10 and the vital sign detecting device 9 in the current hemodialysis treatment, so as to be displayed on the display 13 together with the other values. In such an embodiment, changes in prior and current values of the $\Delta$BV are efficiently and effectively compared to each other to perform an effective hemodialysis treatment.

Specifically, it is preferable to obtain, based on the prior detected values stored in the memory, an ideal range of changes in the $\Delta$BV in the current hemodialysis treatment, and display a maximum value Ma and a minimum value Mi of the ideal range in the same grid indicating currently detected values of $\Delta$BV. In this regard, the ideal range is determined by a medical staff, taking into consideration factors including changes in prior detected values of the $\Delta$BV, complaints by the patient, an additional treatment applied, and results of hemodialysis (e.g., values relating to the ultrafiltration and blood tests).

Accordingly, because the ideal range of the changes in the $\Delta$BV is obtained based on the prior detected values of $\Delta$BV stored in the memory, and maximum values Ma and minimum values Mi of the ideal range are displayed in the same grid indicating the currently detected values of the $\Delta$BV, it is effectively monitored in real-time whether the currently detected values of the $\Delta$BV are within the ideal range, and effectively compared to the values detected by the vital sign detecting device 9.

Further, when the prior detected values are displayed, only predicted values or fair values of the $\Delta$BV may be displayed on the screen 13a. Also, the ideal range of the changes in the $\Delta$BV may be displayed as a band graph having a width from the maximum to minimum values of the ideal range. In addition, a regression curve may be obtained based on the changes in the $\Delta$BV detected in more than one prior hemodialysis treatment, and displayed on the same grid indicating the other values described above.

Moreover, according to this embodiment, the $\Delta$BV value is calculated and detected, based on the hematocrit value Ht detected by the hematocrit sensor 5. However, the $\Delta$BV value may be calculated and detected based on other parameters. In addition, other than the blood pressure and the pulse of the patient as described above, the vital sign detecting device 9 may detect other parameters as long as those parameters are vital signs of the patient.

Furthermore, according to this embodiment, the values detected by the above-described devices are displayed in graphs on the screen 13a. However, charts or tables having time axes aligned with each other may be displayed on the screen 13a. In addition, the length of the time axis or the lengths of the time axes may be standardized to show the duration of time in relation to the duration of a hemodialysis treatment, by setting a predetermined length or lengths for the time axis or axes, respectively, in relation to the width of the screen 13a of the display 13. For example, if the duration of the hemodialysis treatment is longer than the predetermined length of the time axis, then the time axis for the duration is reduced. Similarly, if the duration of the hemodialysis treatment is shorter than the predetermined length of the time axis, then the time axis for the duration is extended. Also, although the screen 13a of the display 13 is a touch panel screen, the display 13 may be provided with a screen other than the touch panel screen (e.g., a non touch panel LCD screen).

Obviously, numerous modifications and variations of the present invention are possible in light of the above teachings. It is therefore to be understood that within the scope of the appended claims, the invention may be practiced otherwise than as specifically described herein.

What is claimed is:

1. A hemodialysis treatment apparatus comprising:
    a circulating blood volume variation rate detecting device configured to detect a circulating blood volume variation rate of a patient in a time-course of a hemodialysis treatment;
    a vital sign detecting device configured to detect a vital sign value of the patient in the time-course of the hemodialysis treatment;
    a memory storing a previous circulating blood volume variation rate of the patient in a time-course of a previous hemodialysis treatment; and
    a display provided with a screen and configured to display the circulating blood volume variation rate and the previous circulating blood volume variation rate in a same grid and the vital sign value in a separate grid on the screen along at least one time scale, the hemodialysis treatment apparatus dialyzing and ultrafiltrating extracorporeally circulating blood of the patient to perform the hemodialysis treatment.

2. The hemodialysis treatment apparatus according to claim 1, further comprising:
    a hemodialysis condition detecting device configured to detect a hemodialysis condition value in the time-course of the hemodialysis treatment, the hemodialysis condition relating to hemodialysis and ultrafiltration in the hemodialysis treatment, wherein
    the screen displays the hemodialysis condition value together with the circulating blood volume variation rate and the vital sign value, along the at least one time scale.

3. The hemodialysis treatment apparatus according to claim 2, wherein:

the at least one time scale is at least one time axis horizontally positioned in at least one grid; and the screen displays the circulating blood volume variation rate, the vital sign value and the hemodialysis condition value in graphs, along the at least one time axis in the at least one grid.

4. The hemodialysis treatment apparatus according to claim 3, wherein the screen displays at least two of the circulating blood volume variation rate, the vital sign value and the hemodialysis condition value in graphs, along a single time axis horizontally positioned in a single grid.

5. The hemodialysis treatment apparatus according to claim 4, wherein the screen displays all of the circulating blood volume variation rate, the vital sign value and the hemodialysis condition value in graphs, along a single time axis horizontally positioned in a single grid.

6. The hemodialysis treatment apparatus according to claim 1, wherein the screen displays an occurrence of an external event affecting the hemodialysis treatment for the patient so that the occurrence is compared to the circulating blood volume variation rate and the vital sign value displayed on the screen.

7. The hemodialysis treatment apparatus according to claim 1, wherein the screen displays, along the at least one time scale, the prior detected circulating blood volume variation rate together with the circulating blood volume variation rate and the vital sign value detected in a time-course of a current hemodialysis treatment.

8. The hemodialysis treatment apparatus according to claim 7, wherein:

an ideal range of the circulating blood volume variation rate in the current hemodialysis treatment is obtained based on the prior detected circulating blood volume variation rate; and the screen displays, along the at least one time scale, a maximum value and a minimum value of the ideal range together with the circulating blood volume variation rate and the vital sign value detected in the time-course of the current hemodialysis treatment.

9. The hemodialysis treatment apparatus according to claim 1, wherein the previous circulating blood volume variation rate is at least one of a maximum value and minimum value.

10. A method for hemodialysis treatment, comprising the steps of:

dialyzing and ultrafiltrating extracorporeally circulating blood of a patient to perform a hemodialysis treatment;

detecting a circulating blood volume variation rate of the patient in a time-course of the hemodialysis treatment;

detecting a vital sign value of the patient in the time-course of the hemodialysis treatment;

retrieving, from a memory, a previous circulating blood volume variation rate of the patient in a time-course of a previous hemodialysis treatment and displaying the circulating blood volume variation rate and the previous circulating blood volume variation rate in a same grid and the vital sign value in a separate grid on a screen of a display along at least one time scale.

* * * * *